(12) United States Patent
Derakhshani et al.

(10) Patent No.: US 9,665,784 B2
(45) Date of Patent: May 30, 2017

(54) SYSTEMS AND METHODS FOR SPOOF DETECTION AND LIVENESS ANALYSIS

(71) Applicant: EyeVerify Inc., Kansas City, MO (US)

(72) Inventors: Reza R. Derakhshani, Shawnee, KS (US); Joel Teply, Shawnee, KS (US)

(73) Assignee: EyeVerify Inc., Kansas City, MO (US)

( * ) Notice: Subject to any disclaimer, the term of this patent is extended or adjusted under 35 U.S.C. 154(b) by 0 days.

(21) Appl. No.: 15/169,107

(22) Filed: May 31, 2016

(65) Prior Publication Data

US 2016/0371555 A1    Dec. 22, 2016

Related U.S. Application Data

(60) Provisional application No. 62/180,481, filed on Jun. 16, 2015.

(51) Int. Cl.
| | |
|---|---|
| *G06K 9/00* | (2006.01) |
| *G01S 7/539* | (2006.01) |
| *A61B 5/1171* | (2016.01) |
| *G01S 15/06* | (2006.01) |
| *G06K 9/62* | (2006.01) |
| *G10L 21/0264* | (2013.01) |

(52) U.S. Cl.
CPC ......... *G06K 9/00906* (2013.01); *G01S 7/539* (2013.01); *G06K 9/00228* (2013.01); *A61B 5/1176* (2013.01); *G01S 15/06* (2013.01); *G06K 9/00255* (2013.01); *G06K 9/00892* (2013.01); *G06K 9/6293* (2013.01); *G06K 2009/00939* (2013.01); *G10L 21/0264* (2013.01)

(58) Field of Classification Search
CPC . G06K 9/00906; G06K 9/00228; G01S 7/539
See application file for complete search history.

(56) References Cited

U.S. PATENT DOCUMENTS

| | | |
|---|---|---|
| 8,978,117 B2 | 3/2015 | Bentley et al. |
| 9,231,765 B2 | 1/2016 | Flautner et al. |
| 9,251,427 B1 * | 2/2016 | Chu ................... G06K 9/00221 |
| 2013/0102283 A1 | 4/2013 | Lau et al. |
| 2013/0198832 A1 | 8/2013 | Draluk et al. |
| 2013/0324081 A1 | 12/2013 | Gargi et al. |

(Continued)

OTHER PUBLICATIONS

Miao et al, "Human Face Classification Using Ultrasonic Sonar Imaging", 2009, Japanese Journal of Applied Physics 48 (2009) 07GC11, pp. 1-5.*

(Continued)

*Primary Examiner* — David F Dunphy
(74) *Attorney, Agent, or Firm* — Goodwin Procter LLP

(57) ABSTRACT

Spoof-detection and liveness analysis is performed using a software-based solution on a user device, such as a smartphone having a camera, audio output component (e.g., earpiece), and audio input component (e.g., microphone). One or more audio signals are emitted from the audio output component of the user device, reflect off a target, and are received back at the audio input component of the device. Based on the reflections, a determination is made as to whether the target is comprised of a three-dimensional face-like structure and/or face-like tissue. Using at least this determination, a finding is made as to whether the target is likely to be spoofed, rather than a legitimate, live person.

21 Claims, 6 Drawing Sheets

(56) References Cited

U.S. PATENT DOCUMENTS

| | | | |
|---|---|---|---|
| 2014/0198620 A1* | 7/2014 | Prausse | G01S 7/521 |
| | | | 367/100 |
| 2014/0372762 A1 | 12/2014 | Flautner et al. | |
| 2015/0186711 A1* | 7/2015 | Baldwin | G06K 9/00228 |
| | | | 382/118 |
| 2015/0294108 A1 | 10/2015 | Kim et al. | |
| 2016/0007935 A1* | 1/2016 | Hernandez | A61B 5/7278 |
| | | | 600/301 |

OTHER PUBLICATIONS

U.S. Appl. No. 14/672,629, filed Mar. 30, 2015, Bio Leash for User Authentication, Derakhshani, et al.

Anjos, A. and Marcel, S., "Counter-measures to Photo Attacks in Face Recognition: A Public Database and a Baseline," Int'l Joint Conf. on Biometrics; pp. 1-7; Oct. 2011.

Bao, et al. "A Liveness Detection Method for Face Recognition Based on Optical Flow Field," 2009 Int'l Conf. on Image Analysis and Signal Processing; pp. 233-236; Apr. 2009.

Bharadwaj, et al., "Computationally Efficient Face Spoofing Detection with Motion Magnification," 2013 IEEE Conf. on Computer Vision and Pattern Recognition Workshops; pp. 105-110; Jun. 2013.

Chingovska, et al., "On the Effectiveness of Local Binary Patterns in Face Anti-Spoofing," Proc. Of the Int'l Conf. BIOSIG; pp. 1-7; Sep. 2012.

Cho, et al., "Real-time Iris Localization for Iris Recognition in Cellular Phone," 6th Int'l Conf. on Software Eng., Artificial Intelligence, Networking and Parallel/Distributed Computing; pp. 254-259; May 2005.

De Freitas Pereira, et al., "Can Face Anti-Spoofing Countermeasures Work in a Real World Scenario?," 2013 Int'l Conf. on Biometrics (ICB); pp. 1-8; Jun. 2013.

De Freitas Pereira, et al., "LBP-TOP Based Countermeasure Against Face Spoofing Attacks," Int'l Workshop on Computer Vision with Local Binary Pattern Variants (ACCV)—Lecture Notes in Computer Science ; 7728:121-132; Nov. 2012.

Evans, et al., "Guest Editorial: Special Issue on Biometric Spoofing and Countermeasures," IEEE Trans. Information Forensics and Security; 10(4):699-702; Apr. 2015.

Galbally, et al., "Image Quality Assessment for Fake Biometric Detection: Application to Iris, Fingerprint, and Face Recognition," IEEE Transactions on Image Processing; 23(2): 710-724; Nov. 2013.

Google Patents, "Cardiac performance monitoring system for use with mobile communications devices (U.S. Pat. No. 8,700,137B2)," accessed on the internet at http://www.google.com/patents/US8700137; downloaded May 24, 2016; 39pgs.

Google Patents, "Facial Recognition (U.S. Pat. No. 8,457,367B2)," accessed on the internet at http://www.google.com/patents/US8457367; downloaded May 24, 2016; 42pgs.

Hernandez, et al., "Biophone: Physiology Monitoring from Peripheral Smartphone Motions," 2015 37th Annual Int'l Conf. of the IEEE Engineering in Medicine and Biology Society (EMBC); pp. 7180-7183; Aug. 2015.

Int'l Business Times, "Android Jelly Bean Face Unlock 'Liveness Check' Bypassed with Photo Editing," accessed on the internet at http://www.ibtimes.co.uk/androidjel-lybeanfaceunlockhackedphotoediting370426; downloaded May 24, 2016; 3pgs.

Int'l Search Report and Written Opinion of the ISA/EP in PCT/US2015/023344; 14pgs.; Sep. 16, 2015.

Kollreider, et al., "Real-Time Face Detection and Motion Analysis with Application in 'Liveness' Assessment," IEEE Transactions on Information Forensics and Security; 2(3):548-558; Sep. 2007.

Li, et al., "Live Face Detection Based on the Analysis of Fourier Spectra," SPIE Proceedings: Biometric Technology for Human Identification; 5404:296-303; Aug. 2004.

McKerrow, et al., "Classifying Still Faces with Ultrasonic Sensing," J. Robotics and Autonomous Systems; 55(9):702-710; Sep. 2007.

Motorola Mobility, Inc., "Motorola Defy+ with Motoblur," accessed on the internet at https://motorola-global-enaus.custhelp.com/ci/fattach/get/588640/1360689155/redirec/1/filename/defy_plus_ug_au_en_68016355001_v3.pdf; downloaded Jun. 25, 2015; 70pgs.

Sun, et al., "Blinking-based Live Face Detection Using Conditional Random Fields," International Conference on Advances in Biometrics—Lecture Notes in Computer Science; 4642:252-260; Aug. 2007.

Tabula Rasa, "Trusted Biometrics under Spoofing Attacks," accessed on the internet at http://www.tabularasa-euproject.org; downloaded May 24, 2016; 2pgs.

Tan, et al., "Face Liveness Detection from a Single Image with sparse Low Rank Bilinear Discriminative Model," 11th European Conf. on Computer Vision—Lecture Notes in Computer Science ; 6316:504-517; Sep. 2010.

Wang, et al., "Exploiting Spatial Redundancy of Image Sensor for Motion Robust rPPG," IEEE Transactions on Biomedical Engineering; 62(2):415-425; Feb. 2015.

Wen, et al., "Face Spoof Detection with Image Distortion Analysis," IEEE Trans. Information Forensics and Security; 10(4):746-761; Apr. 2015.

Zhang, et al., "A Face Anti-Spoofing Database with Diverse Attacks," 5th IAPR Int'l Conf. on Biometrics (ICB); pp. 26-31; Mar. 2012.

Zhenwei, et al., "Human Face Classification Using Ultrasonic Sonar Imaging," Japanese J. Appl. Phys.; 48(7S):07GC11; Jun. 2009.

Guillaume, G., et al., "Face Detection Method Based on Photoplethysmography," 2013 10th IEEE Int'l Conf. on Advanced Video and Signal Based Surveillance (AVSS); pp. 449-453; Aug. 27, 2013.

Int'l Search Report and Written Opinion of the ISA/EP in PCT/US2016/035007; 12pgs.; Aug. 19, 2016.

Kose, N., et al., "Countermeasure for the Protection of Face Recognition Systems Against Mask Attacks," 10th IEEE Int'l Conf. on Automatic Face and Gesture Recognition (FG2013); 6pgs; Apr. 22-26, 2013.

\* cited by examiner

SYSTEMS AND METHODS FOR SPOOF DETECTION AND LIVENESS ANALYSIS

CROSS-REFERENCE TO RELATED APPLICATION

This application claims priority to and the benefit of U.S. Provisional Patent Application No. 62/180,481, filed on Jun. 16, 2015, and entitled "Liveness Analysis Using Vitals Detection," the entirety of which is incorporated by reference herein.

TECHNICAL FIELD

The present disclosure generally relates to image, sonic signal, and vibrational signal analysis and, in particular, to image and signal processing techniques for detecting whether a subject depicted in an image is alive.

BACKGROUND

It is often desirable to restrict access to property or resources to particular individuals. Biometric systems can be used to authenticate the identity of an individual to either grant or deny access to a resource. For example, iris scanners can be used by a biometric security system to identify an individual based on unique structures in the individual's iris. Such a system can erroneously authorize an impostor, however, if the impostor presents for scanning a pre-recorded image or video of the face of an authorized person. Such a fake image or video can be displayed on a monitor such as a cathode ray tube (CRT) or liquid crystal display (LCD) screen, in glossy photographs, etc., held in front of a camera used for scanning. Other spoofing techniques include the use of a photographically accurate three-dimensional mask of a legitimate user's face.

One category of existing anti-spoofing measures focuses primarily on static imagery (e.g., photograph based) attacks. These measures assume that static spoof attacks fail to reproduce naturally occurring and disparate movement of different parts of the image, mostly within the face. They also assume that each of the aforesaid motions in live scans occurs at a different scale in terms of the natural agility and frequency of the associated muscle groups. However, these measures can only detect static (e.g., picture-based) spoof attacks, and need a certain time window of observation at a high enough frame rate to be able to resolve the aforesaid motion vectors to their required velocity and frequency profiles, if any. They can also falsely reject live subjects that are holding very still during the scan, or falsely accept static reproductions with added motion, e.g., by bending and shaking the spoofing photos in certain ways.

A second category of existing anti-spoofing measures assumes that the photographic or video reproduction of the biometric sample is not of sufficient quality and thus image texture analysis methods can give identify the spoof. However, the assumption of discernibly low quality spoof reproduction is not a reliable one, especially with the advent of advanced high quality and exceedingly commonplace high definition recording and display technologies that can even be found in modern smartphones and tablets. Not surprisingly, by relying on specific and technology-dependent spoof reproduction artifacts, such techniques have been shown to be dataset dependent and have demonstrated subpar generalization capabilities. Another category of anti-spoofing measures, related to the second, which is based on reference or no-reference image quality metrics, suffers from the same shortcomings.

SUMMARY

In various implementations described herein, the detection of physical properties indicating the presence of a live person is used to distinguish live, authentic faces from images/videos, verifications made under duress, and other spoofed and fraudulent authentication methods, and/or to identify spoofs, such as by detecting the presence of devices used to playback recorded images/videos/other physical reconstructions of the legitimate user for spoofing a biometric system. This is achieved, in part, by (a) detecting signatures of spoofs and (b) verifying the liveness and physical presence of an individual using three-dimensional face detection and two-factor pulse identification.

Accordingly, in one aspect a computer-implemented method includes the steps of: emitting, using an audio output component of a user device, one or more audio signals; receiving, using an audio input component of the user device, one or more reflections of the audio signals off a target; determining, based on the one or more reflections, whether the target comprises at least one of a face-like structure and face-like tissue; and determining whether the target is a spoof based at least in part of the determination of whether the target comprises at least one of a face-like structure and face-like tissue. The user device can be, for example, a mobile device including a smartphone, a tablet, or a laptop. The one or more audio signals can include short coded pulse pings, short term chirps, or CTFM pings. One or more characteristics of the one or more audio signals can be randomized.

In one implementation, the method further includes the steps of: training a classifier to identify physical features of the target; and providing as input to the classifier information based on the one or more reflections of the audio signals off the target, wherein the determination of whether the target is a spoof is further based at least in part on an output of the classifier received in response to the provided input.

In another implementation, the method further includes the steps of: receiving a plurality of images of the target; and determining, based on detected light reflections in the images, whether the target comprises a three-dimensional face-like structure.

In a further implementation, the method further includes the steps of: receiving a plurality of images of the target; and identifying, based on the images, whether the target has a first pulse, wherein the determination of whether the target is a spoof is further based at least in part on the identification of whether the target has a pulse. The first pulse can be identified using remote photoplethysmography.

In yet another implementation, a second pulse of the target is identified through physical contact with the target, wherein the determination of whether the target is a spoof is further based at least in part on the measurement of the second pulse. A determination can be made as to whether the second pulse correlates to the first pulse, wherein the determination of whether the target is a spoof is further based at least in part on the correlation. Measuring the second pulse can include receiving information associated with the second pulse from the user device or another handheld or wearable device. The information associated with the second pulse can include a ballistocardiographic signal.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
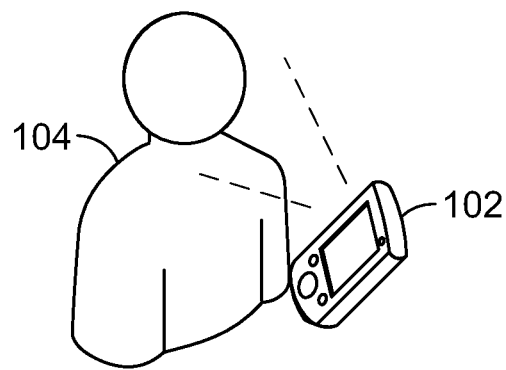
FIGS. 1A-1C depict various use cases for anti-spoofing and liveness detection.

Described herein, in various implementations, are systems and accompanying methods for providing a multi-stage, software-based anti-spoofing and "liveness" detection technology that combines sonic three-dimensional (3D) "faceness" sensing using face-modulated sound reflections with multi-source/multi-path vitals detection. As used herein, "liveness" refers to characteristics tending to indicate the presence of a live person (not a spoof or imitation of a live person, such as an image or prerecorded video of an eye or face, three-dimensional modeled head, etc.). Such characteristics can include, for example, recognizable physical properties such as a face, a pulse, a breathing pattern, and so on. "Faceness" refers to characteristics tending to indicate the presence of a real face, such as the actual (as opposed to reproduced) presence of eyes, a nose, a mouth, chin, and/or other facial features and tissue arranged in a recognizable pattern. This definition of faceness can be augmented by including the passive or active sonic, photic, and/or electromagnetic signatures of real faces (as opposed to those of spoof faces).

The present disclosure provides a new physics-based solution that can be implemented entirely in software and, among other things, detects spoofing screen playbacks regardless of their quality. It overcomes the shortcomings of the existing vision based anti-spoofing solutions through evaluating the likelihood of a real 3D face being presented to a user device through examination of its sonic (and/or photometric) signature, all in a fashion transparent to the user. Advantageously, this technique detects spoofs for biometric authentication using only typical mobile phone earpieces/sound transducers and microphones in various everyday environments. Resulting sonic signatures using existing hardware of mobile devices is weak and challenged by multiple confounding factors, which the described methodology overcomes. Sources for the aforementioned poor sonic signal to noise ratio include unwanted echoes, as well as the acoustic path nonlinearities and bandwidth limitations (including those of the transducers), microphone/earpiece directionality and sensitivity, and internal reverberations of the device. Also, given the longer wavelengths of the utilized audio bands, the spatial resolution is reduced compared to existing ultrasonic sonar systems and much of the target reflections are instead dissipated via scattering, providing for the indirect detection of embedded sonic signatures, as detailed herein.

In one implementation, the anti-spoofing and liveness detection technology includes verifying the presence of a three-dimensional face-like structure and measuring the pulse of the target using multiple sources. Three-dimensional face sensing can be performed using face-modulated sound reflections (e.g., from a coded high-pitched probe signal emitted from a phone earpiece or other sound transducer, similar to sonar, with reflections of the signals received a phone microphone or other audio input) and/or structured light photometric stereo (e.g., from fast patterned illuminations from a phone screen). Vital detection, such as the detection of a user's pulse, can be measured from heart pumping action that induces face color changes and hand/body vibrations. Heart rate detection can be accomplished through multiple paths: heartbeat-induced mechanical vibrations of the body, also known as ballistocardiograms, and detection of pulse from skin color changes recorded by a red-green-blue (RGB) camera, also known as remote photoplethysmograms (remote PPG, or rPPG). A user's pulse can also be detected via other wearable/mobile devices with heart rate sensors.

Figure 1B:
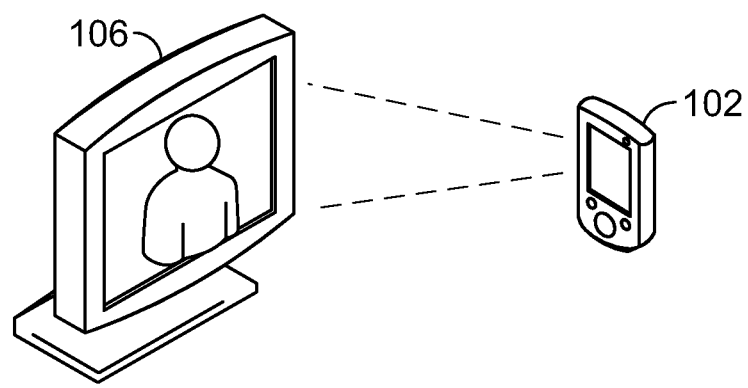
Figure 1C:
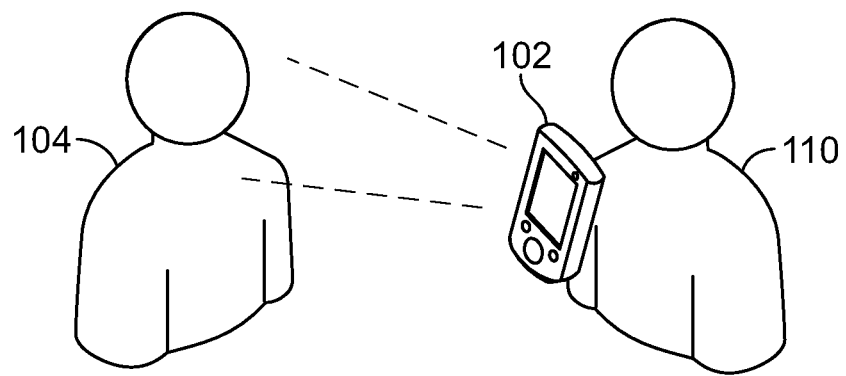

FIG. 1A-1C illustrate various use cases for the anti-spoofing and liveness analysis technology as described herein. For example, in FIG. 1A, a target user 104 uses his mobile device 102 (e.g., smartphone, tablet, etc.) to authenticate himself using a biometric reading (e.g., eye scan) captured by the mobile device camera. In addition to the camera, the mobile device 102 can utilize other sensors, such as an accelerometer, gyroscope, fingertip heartbeat sensor, vibration sensor, audio output component, (e.g., speaker, earpiece, or other sound transducer), audio input component (e.g., microphone), and the like in order to verify the physical presence of the user, using the presently described techniques. In FIG. 1B, the mobile device 106 captures an image or video of a target on an LCD monitor 106 or other display screen. Software executing on the mobile device 102 can determine that the target is not physically present using the present techniques, for example, three-dimensional face detection, evaluation of reflected light and/or sound signals, and pulse detection. FIG. 1C depicts a second user 110 holding the mobile device 102 and directing it at the target user 104. In this instance, although the physical presence of the target user 104 would be established (e.g., by three-dimensional facial structure and visual pulse recognition), a secondary pulse reading taken by the mobile device 102 via physical contact between the device 102 and the second user 110 would not correspond to a visual pulse identified for the target user 104 and, thus, verification of the user's identity would fail.

Other techniques for anti-spoofing and liveness analysis can be used in conjunction with the technology described herein. Such techniques include those described in U.S. patent application Ser. No. 14/480,802, filed on Sep. 9, 2014, and entitled "Systems and Methods for Liveness Analysis," and U.S. patent application Ser. No. 14/672,629, filed on Mar. 30, 2015, and entitled "Bio Leash for User Authentication," the entireties of which are incorporated by reference herein.

Figure 2:
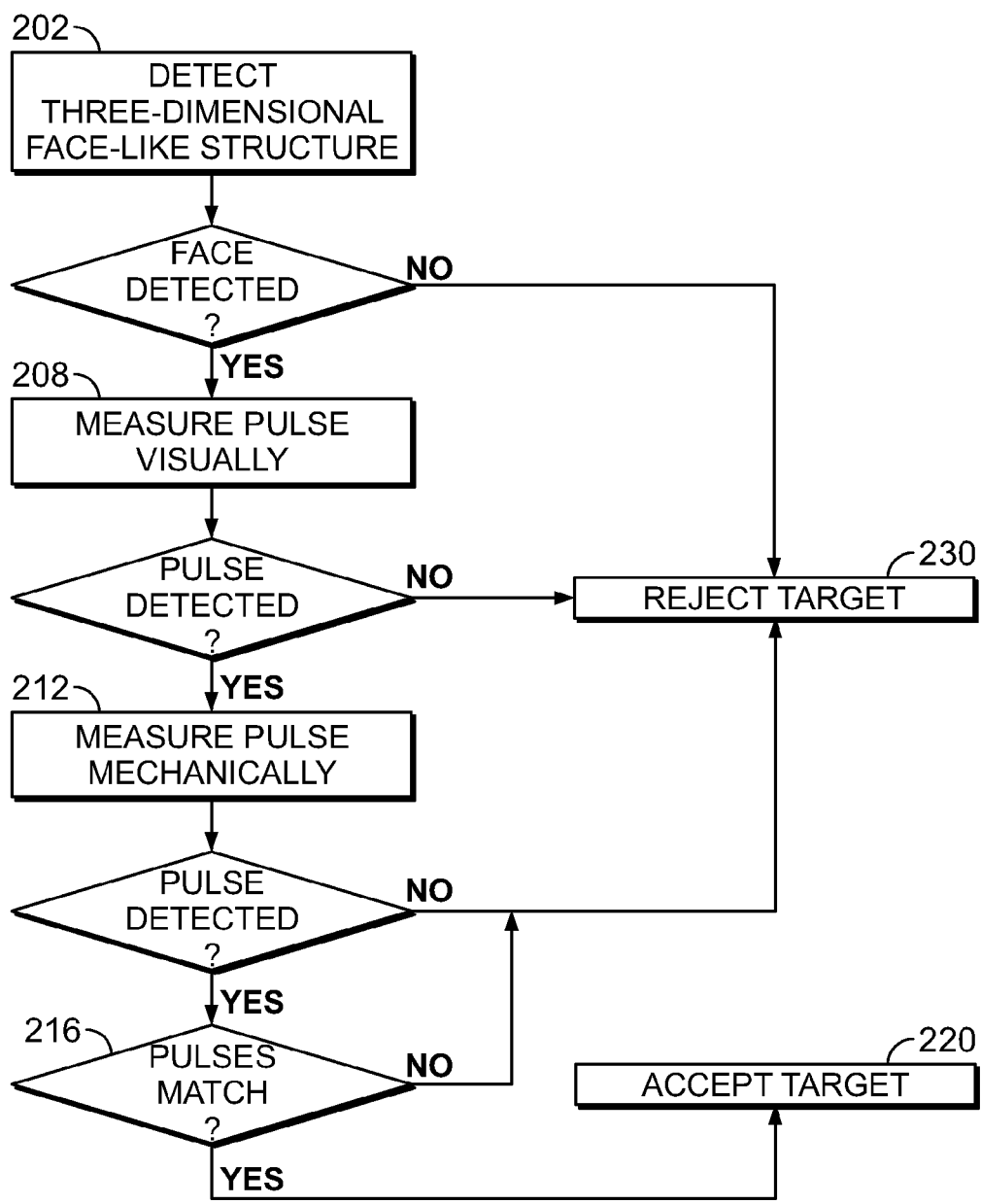
FIG. 2 depicts a method for anti-spoofing and liveness detection according to an implementation.

One implementation of a method for spoof and liveness detection is depicted in FIG. 2. Beginning at STEP 202, a user device (e.g., mobile device 102, or other cell phone, smartphone, tablet, virtual reality device, or other device used in a biometrically-enhanced user interaction, such as logging in to a banking app while using biometric eye verification), detects if a face-like three-dimensional (3D) object is positioned in front of the device, and not a spoof such as a pre-recorded video on a flat display.

The 3D facial detection in STEP 202 can be accomplished using various methods or combinations thereof, and can be based on the availability of certain sensors and transmitters on a user's device. In one implementation, sound waves (e.g., high frequency sound waves) are used to determine whether a three-dimensional face or, alternatively, a flat display or non-face-like 3D object, is being presented to a biometric sensor (for image-based biometrics using a face or any of its sub-regions, including the ocular sub-region, the biometric sensor can include, for example, a mobile device camera). One example of a sonic (sound wave) based technique is continuous transmission frequency modulation (CTFM), in which the distance to different facets/surfaces of a face is measured based on the time-varying frequency of a sonic probe transmitted by a measuring device (e.g., an audio output component (earpiece, speaker, sound transducer) of a device in conjunction with an audio input component (microphone) of the same or a different device). In the case of biometric authentication, the sonic distance measurement can also be used to confirm that the measured interocular distance corresponds to an expected interocular distance that was determined at the time of the target's enrollment. The foregoing is one example of a real-life scale measurement check, although it will be appreciated that other device-to-face distance measurements, such as those coming from camera's focus mechanism, can also be used. Techniques for 3D facial detection are described in further detail, below.

In another implementation, the existence and extent of photometric stereo is analyzed for characteristics tending to indicate the presence of a three-dimensional face-like object. The validity of photometric effects can also be combined with the earlier-mentioned sonic-measured distances and, optionally, compared with photometric stereo data gathered during a biometric enrollment phase. Photic measurements can use aliasing to work with cameras that have lower frame rates if the device screen can be driven at a higher frame rate, making the temporal variations of the screen-induced photic probe more imperceptible to the user. Note that, if the aforesaid three-dimensional characteristics are measured with higher accuracy, 3D profiles of the user face, as determined using sonic and/or photometric measurements at the time of valid enrollment, can become user-specific to a certain extent and can induce more specificity (as soft biometrics) into the anti-spoofing measures described herein.

If a face-like 3D structure is detected, the device can optionally further verify liveness by detecting if the face-like structure has a pulse that is present and within an expected range (using, e.g., facial rPPG based on images captured by a device camera) (STEP 208). Otherwise, if no 3D facial structure is detected, the liveness rejection fails and the target is rejected (STEP 230). If a valid pulse is detected, then a 3D face-like object with apparent circulation has been established as the first phase of liveness detection and anti-spoofing. This phase limits spoof attacks to face-like 3D structures with pulsating skin amenable to bypassing rPPG, which is a high bar.

In a secondary phase, the system can optionally attempt to correlate the primary detected pulse from the face-like structure (e.g., face rPPG after sonic and/or photometric 3D face check) with a second pulse measurement obtained through a different method for stronger liveness detection/anti-spoofing (STEPS 212 and 216). Secondary pulse measurement can be accomplished, e.g., through ballistocardiogram signals, which can be captured based on hand-held device shakes induced by heart-pumping action and measured by device motion sensors, or a pulse-sensing wearable, if available, or other suitable secondary path for checking the heart rate or its harmonics. If no secondary pulse is detected or the secondary pulse is otherwise invalid (e.g., falls outside of an expected range), or if the correlation fails (e.g., the system detects that the pulses do not match in rate or other characteristics), the target is rejected (STEP 230). Conversely, if the foregoing steps verify liveness, the target can be accepted as a live, legitimate user (STEP 220). It should be appreciated that the verification phases described in this implementation need not be performed in the order described; rather, alternative ordering of steps is also contemplated. For example, one or more pulse measurements can be taken first, with 3D facial detection used to strengthen a conclusion of liveness vs. spoof determined based on the pulse measurements. Further, not all steps need be performed (e.g., a determination of whether a spoof exists can be made solely on the 3D facial detection).

Sonic 3D Faceness Measurement

This sonic technique detects whether there is a face (expected for legitimate device-facing eye or face biometric scanning) or other structurally non-face like object (e.g., a flat screen or other spoofing scenario) that is being displayed to a biometric sensor (e.g., the front-facing camera of a mobile phone). The technique is used for image-based biometrics using the face or its sub-regions, including ocular sub-regions. Examples of sonic pings that can be used for 3D faceness measurement include, but are not limited to, short coded pulse pings, short term chirps, and CTFM.

Short coded pulse pings include those pings where maximal correlation codes (e.g., Barker 2 through Barker 13 patterns, be it in their original form or binary phase shift keying coded) and/or short term chirps (e.g., linear frequency sweeps with an envelope such as a Kaiser window) are sent through an audio output component, such as a phone earpiece or other onboard sound transducer. If multiple audio output components exist, acoustic beam forming can be used to better spatially focus the sonic ping. Matched filter or autocorrelation decoding of the echoes from the aforesaid pulse compression techniques allows for reconstruction of the target's coarse 3D signature (which also reflects its texture and material structure due to acoustic impedance of the impacted facets). This information is presented to a user device through time of flight and morphology of the received echo, similar to what is seen in sonar and radar systems. Matched filter entails cross correlation of the received echo with the original ping signal. Auto correlation of the echo with itself can be used instead, where an immediate received copy of the ongoing signal effectively becomes the detecting template. In either case, further post processing, such as calculation of the amplitude of the analytical version of the decoded signal, is performed prior to feature selection and classification.

For CTFM pings, the distance from different facets/surfaces of the target (here, the user's face or a spoofing screen) is measured based on the time-varying frequency of the high pitched sonic probe transmitted by the device (e.g., through the earpiece of a phone).

In some implementations, the sonic distance measurement is also used to check the overall face distance to ensure proper correspondence to expected interocular distance measured via imaging at the time of biometric enrollment (real life scale measurement check). In some implementations, low signal to noise ratio of the echo can be further overcome by averaging multiple pings and/or multi-microphone beam forming and noise cancellation.

It should be noted that there are two aspects this technique: (i) rejection of non-face objects (e.g., spoofing screens), and (ii) acceptance of face-like 3D sonic profiles, especially those that are similar to those of the registered user (e.g., user-specific sonic face templates created during enrollment), increasing anti-spoofing accuracy by accounting for subject-specificity. The latter aspect utilizes the learning of face signatures from sonic reflections (presentation learning), which can be performed using well-known machine learning techniques, such as classifier ensembles and deep learning. The accuracy of the sonic 3D face profile recognition can be further increased by including assistive signals from an image sensor. For instance, the echo profiles will change if the user is wearing glasses or covering part of their face with a scarf. Image analysis can reveal these changes and adjust the classification modules accordingly, for instance, by using appropriate templates and thresholds for those circumstances.

Photometric 3D Faceness Measurement

In some implementations, following sonic face structure detection (or before or simultaneously with sonic face structure detection), the 3D faceness measure is further reinforced by examining the existence and extent of facial 3D structure from interrogating lighting variations, such as photometric stereo as induced by high frequency patterns of a mobile device screen coded with illumination intensity, phase and frequency, and color (structured screen lighting). Photometric stereo effects are generally dependent on the light source distance and, thus, can be combined with the earlier-mentioned sonar measured distances.

In further implementations, the verification photometric signatures can be compared with one or more photometric signatures derived during enrollment of a user, in order to make these measurements subject-specific for higher sensitivity and specificity. By combining the improved sonic and photometric 3D face profiling, the combination not only can detect spoofs with better accuracy while continuing to avoid rejection of the real users, but also detect user-specific sonic-photometric face signatures as a soft biometric and, thus, further increase performance of the primary biometric modality as an added soft identification modality.

Photic measurements can also take advantage of imaging sensor aliasing for a better user experience if, for example, the device screen can be driven at a higher frame rate to make the temporal variations of the screen-induced photic probe more imperceptible. That is, if the camera is driven at a lower frame rate than the screen, one can use the aliased frequency component of the structured light and proceed normally.

Cardiac Measurement

In some implementations, if faceness is sonically and/or photometrically validated, the existence (and, in some instances, the value) of a facial pulse can be detected/measured from the front-facing camera of a mobile device in a period of observation time that is shorter than what is needed for a full rPPG pulse rate calculation. This quick check limits spoof attacks to face-like 3D structures with pulsating skin, which is very a high bar. This pulse identification step can serve as a supplemental layer of anti-spoofing protection after the sonic (and, optionally, photometric) faceness measurement.

In further implementations, for an even stronger liveness check, the proposed method measures and cross-validates the user's multi-path cardiac vitals. One cardiac signal can be determined based on, for example, the earlier-mentioned 3D-validated-face rPPG. Additional cardiac signals (or their major harmonics) can be recovered from ballistocardiogram signals (e.g., hand-held device vibrations and their harmonics as induced by the heart's mechanical pumping action and measured by device motion sensors, and optionally corroborated by correlated small vibrations detected from device camera feeds after rigorous signal processing and motion amplification). These additional cardiac signals can be acquired by other heart rate sensors when available, such as health monitoring wearables or other heart rate sensors embedded in the user's mobile device. In some implementations, motion sensor signals are preprocessed by band-pass filtering in targeted heart rate frequency ranges and their harmonics. In other implementations, heart rate harmonics are used as the primary ballistocardiogram signals. In further implementations, the ballistocardiogram is augmented by amplified correlated cardio-induced motion as seen by, e.g., the camera of the mobile device.

Upon detection of a pulse and a significant real-time correlation between multiple cardiac signals (e.g., the rPPG and ballistocardiogram pulse measurements), a stronger probability of liveness can be guaranteed. Such a cardiac-loop liveness score can be, for example, the real-time correlation/similarity strength between the two cardiac signals (ballistocardiogram and rPPG). This additional layer of anti-spoofing closes the cardiac liveness verification loop, from the holding hand (mechanical path) to the perceived validated face/eye (optical and acoustic paths) using the heartbeat of the user seeking biometric verification.

The presently described technology can incorporate various techniques for heart rate detection that are known in the art and are described in, for example, U.S. Pat. No. 8,700,137, issued on Apr. 14, 2014, and entitled "Cardiac Performance Monitoring System for Use with Mobile Communications Devices"; "Biophone: Physiology Monitoring from Peripheral Smartphone Motions," Hernandez, McDuff, and Picard, Engineering in Medicine and Biology Society, 2015 37th Annual International Conference of the IEEE, 2015; and "Exploiting Spatial Redundancy of Image Sensor for Motion Robust rPPG," Wang, Stuijk, and de Haan, IEEE Transactions on Biomedical Engineering, vol. 62, no. 2, February 2015, the entireties of which are incorporated by reference herein.

Additional Implementations

Figure 3:
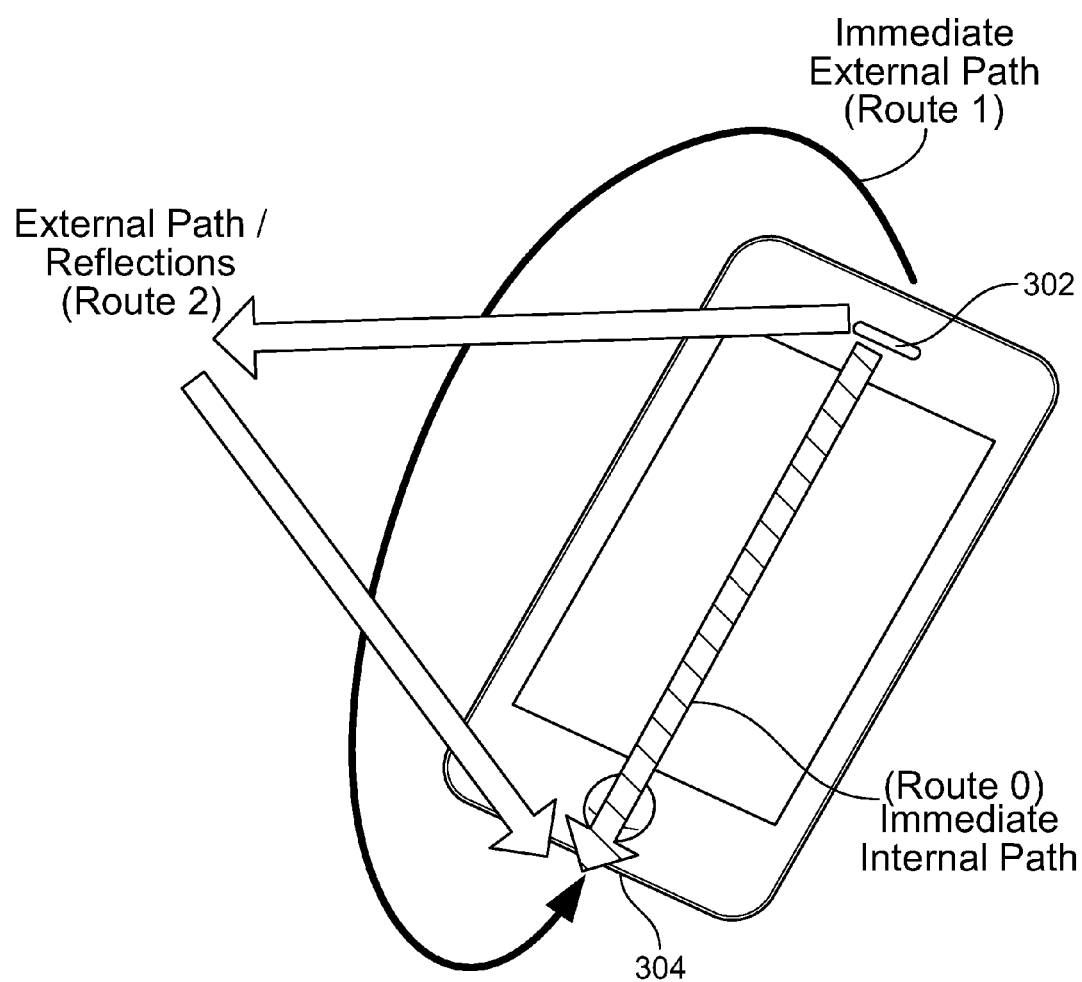
FIG. 3 depicts example direct and indirect acoustic paths for a sonic probe pulse between a phone earpiece and microphone.

Referring now to FIG. 3, during a biometric scan of a user's face and/or ocular regions with a front-facing camera, according to the techniques described herein, a phone earpiece 302 (and/or other acoustic transducers, including multiple speakers in a beam forming arrangement focused on the targeted facial areas) emits a series of signals to acoustically interrogate faceness of the perceived interacting user. The phone microphone(s) 304 collects the reflections of the signal, mostly from the face, in the event of live authentication. However, it is possible that a screen or other reproduction of the face is presented instead during a spoof attack. In some implementations, where the device's bottom microphone 304 is used, the onset of probe signal emission is detected through time stamping of the first transmission heard by the microphone 304 as the first and loudest received copy of the acoustic probe (Route 0), given the speed of sound and the acoustic impedance as the ping travels through/across the phone body. The original signal is used in conjunction with its echo as received by the phone's microphone 304 for matched filtering (can include signal/echo received via external Route 1, in which the signal propagates through the air from the earpiece 302 to the microphone, and external Route 2, in which the signal reflects off the target and is received by the microphone 304). Examples of the acoustic ping include pulse compression and/or maximal correlation sequences such as short chirps or Barker/M-sequence codes.

In some implementations, if available, a front facing microphone is used for improved directionality, background noise suppression, and probe signal departure onset detection. Directional polar patterns of a device microphone, such as Cardioid, can be selected for better directional reception. Multiple microphones on the device, if available, can be used for beam forming for better directionality and, thus, better reception of the faceness echo.

In some implementations, the autocorrelation of the reflected sound is used for decoding the face/spoof echo component of the reflected sound. This method can yield better demodulation, as the matched filter kernel is essentially the actual transmitted version of the probe wave pattern here. In further implementations, the probing signal is of a CTFM type and, hence, heterodyning is used for resolving the spatial profile and distance of the target structure. Ultimately, a classifier can decide perceived faceness based on features extracted from the demodulated echoes from any number of the abovementioned methods Based on the characteristics of the echo as recorded by the device's microphone(s), there are different ways to determine whether the sound was reflected off of the user's face as opposed to a spoofing screen or other spoofing object, noting the specific multifaceted 3D shape of a face and its absorbance/reflectance properties versus that of, e.g., a two-dimensional spoof, such as an LCD reproduction of the facial or ocular regions of interest.

Figure 4:
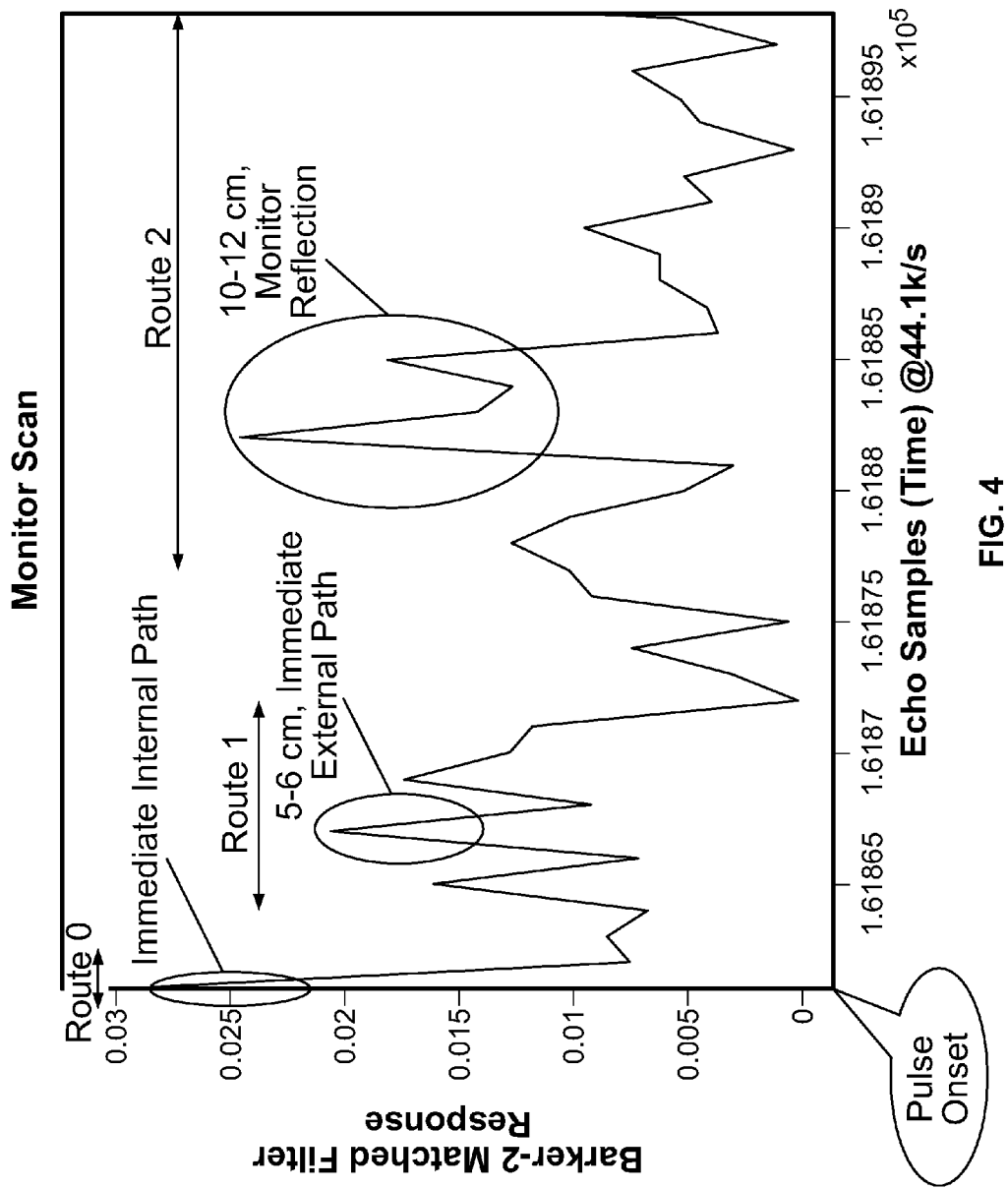
FIGS. 4 and 5 depict example matched-filter demodulated echoes exhibiting reflections for a monitor screen and real face, respectively.
Figure 5:
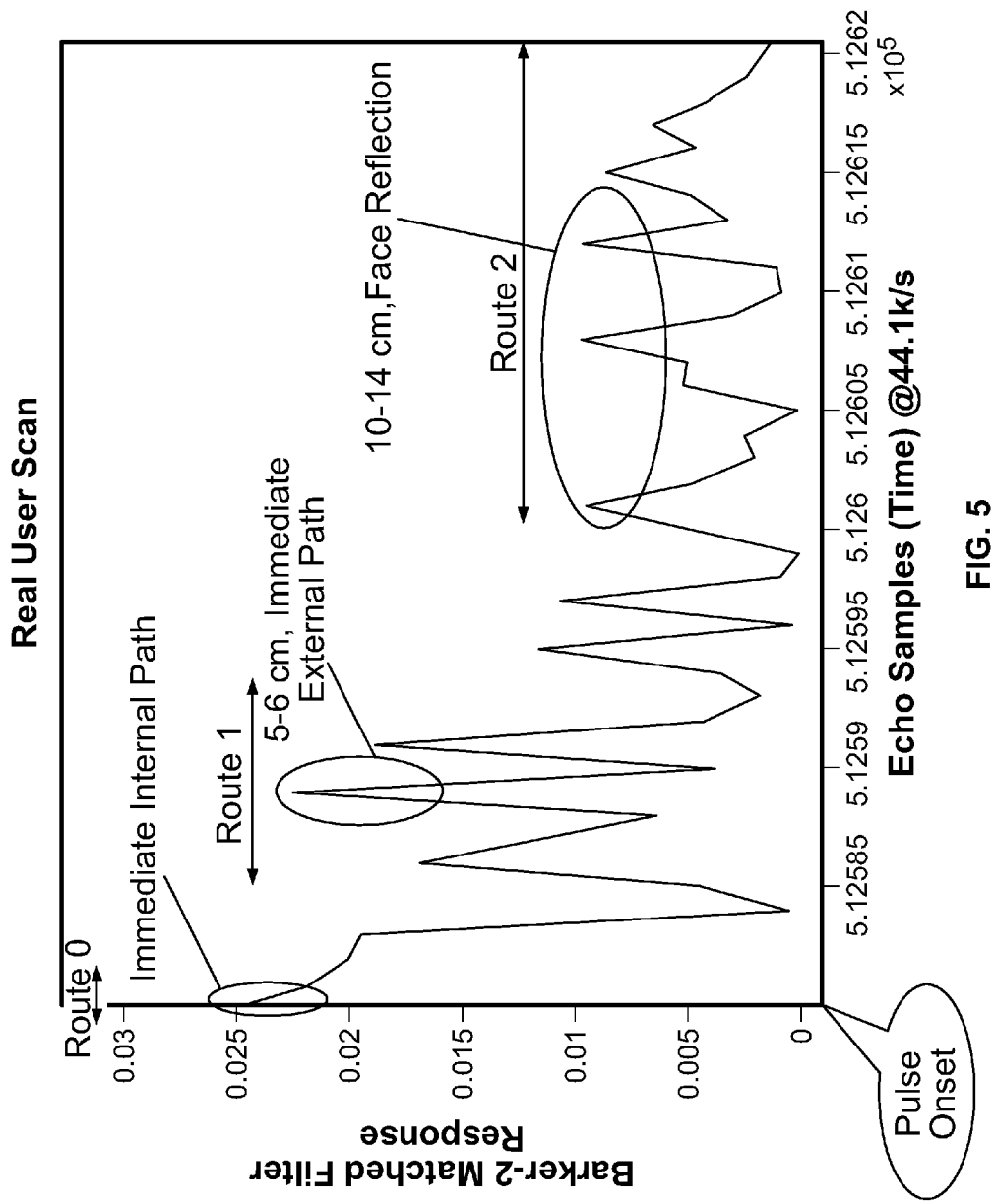

FIGS. 4 and 5 depict example matched-filter demodulated echoes using Barker-2 code sequence for the first 20 cm of the acoustic path flight, where various acoustic reflections through Route 0, 1, and 2 (see FIG. 3) are clearly observed. More particularly, FIG. 4 depicts the reflection caused by a monitor screen approximately 10-12 cm away from the phone emitting the pulse, whereas FIG. 5 depicts the different echo signature caused by a real human face approximately 10-14 cm in front of the phone.

In some implementations, the sonic probe signal is a maximally correlational signal, such as Barker codes of order 2 to 13 (either in their original form or with binary phase-shift keying (BPSK) modulation, where the carrier frequency shifts its phase by 180 degrees for each bit level change), or pseudo random M-sequences. In some implementations, the sonic probe signal is composed of short chirps (of various frequency ranges, and sweeping and amplitude envelopes). The probing signal can be, for example, a CTFM signal. These short, high frequency signals are transmitted from an audio output component, such as an earpiece (in the case of a smartphone or tablet, for example, as it naturally faces the target when using the front facing camera for captures). In some implementations, however, other or multiple device sound transducers are used for beam forming to better concentrate the sonic probe on the biometric target.

The sonic probe signal can take various forms among implementations of the disclosed techniques. For example, in one implementation, the sonic probe signal is a CTFM signal with Hanning-windowed linear chirps sweeping 16 kHz to 20 kHz. In another implementation, the probe signal is a maximally correlational sequence, such as Barker-2 sequence with 180 degree shift sine BPSK at 11.25 kHz carrier frequency sampled at 44100 Hz. In a further implementation, the probe signal is a windowed chirp signal. The chirp can be, for example, a cosine signal with a staring frequency of 11.25 kHz, linearly sweeping to 22.5 kHz in 10 ms, and sampled at 44100 Hz. The windowing function can be a Kaiser window of length 440 samples (10 ms at 44.1 kHz sampling rate), with a Beta value of 6. The foregoing values represent those probe signal parameters providing reasonably accurate results. It is to be appreciated, however, that probe signal parameters that provide accurate results can vary based on device and audio input/output component characteristics. Accordingly, other ranges of values are contemplated for use with the present techniques.

In some implementations, the initial phase, frequency, and the exact playback onset of the emitted probe signal, or even the code type itself, can be randomized (e.g., for a PSK coded Barker probe pulse train) by the mobile biometric module. This randomization can thwart hypothesized (though far reaching and sophisticated) attacks where a reproduced fake echo is played back to the phone to defeat the proposed sonic faceness checker. Because on-the-fly randomized phase/type/onset/frequency of PSK modulation of the coded sonic sequence or other dynamic attributes of the outgoing probe is unbeknownst to the attacker, the hypothetical injected echoes will not be demodulated by the matched filter, nor follow the exact expected patterns.

During basic Barker code/chirp/CTFM procedure, the reflection of the probe signal, delayed in time (and thus frequency for CTFM) based on its roundtrip distance, is recorded by the device's microphone(s) or other audio input component(s). The original chirp or otherwise coded acoustic probe can be detected either by a matched filter or auto-correlation (for Barker and short chirp), or demodulated to baseband by multiplying the echo by the original frequency ramp and taking the lower frequency byproduct (heterodyning). Each impacted facet of the target reflects the probe pulse in a manner related to its textural and structural properties (e.g., acoustic impedance difference between air and the impacted surface, as well as its size and shape), and distance from the sonic source (sound round trip delay). Thus, in its simplistic form (assuming no noise and unwanted background echoes), a face will have multiple reflections at lower magnitudes (as reflected by its multiple major facets at air-skin and soft tissue-bone interfaces), while, for instance, a spoofing monitor screen will have a single stronger reflection (compare FIGS. 4 and 5).

Given the round trip delay of each reflection, the distance of each reflecting target facet can be translated into time delay in matched filter/auto-correlation response or a frequency delta in the Power Spectral Density or PSD (see FIGS. 6 and 7, further described below), providing target-specific echo morphology. To calculate PSD features from CTFM signals, different methods can be used. In some implementations, a multitaper method is applied to a 0-200 Hz span of the demodulated echo, and the binned output is used as the input to a classifier that can be, for example, a linear or Gaussian kernel Support Vector machine, or similar.

More specifically, in various implementations, one or more of the following steps are taken for chirp/coded pulse demodulation and target classification. In one instance, the sonic probe avoids loud acoustic environment noise by checking the microphone readouts frequently (e.g., every 100 ms, every 500 ms, every 1 s, etc.), listening for potentially disrupting noise. This check can include calculating the correlation (convolution with time reversed) chirp/coded-pulse probe signal, and setting the trigger threshold to that obtained in a reasonably quiet environment. In some implementations, an additional similar check is conducted shortly after playing the acoustic probe signal to determine if a disruptive noise occurred right after the sonic ping. If so, the session can be discarded. Multiple chirps can also be averaged (or median-processed) at the signal or decision score level to improve results.

In one implementation, preprocessing involves a high pass filtering of the received signal to only allow for frequencies relevant to the transmitted chirp/coded signal. This high pass filter can be, for example, an equiripple finite impulse response filter with a stopband frequency of 9300 Hz, passband frequency of 11750 Hz, stopband attenuation of 0.015848931925, passband ripple of 0.037399555859, and density factor of 20.

In some implementations, the demodulation includes a normalized cross-correlation of the high-passed received echo with the original sonic chirp/coded signal (equivalent to normalized convolution with time reversed version of the sonic probe). The maximum response is considered the onset/origin of the decoded signal. The demodulation can include, for example, auto-correlation of the portion of the signal 0.227 ms before the above mentioned onset, to 2.27 ms+ the time length of the chirp/coded signal, after the onset marker. Post-processing the demodulated signal can include calculating the magnitude of its analytical signal (a complex helical sequence composed of the real signal plus an imaginary, 90 degrees phase shifted version of it) to further clarify the envelope of the demodulated echo. In one implementation, assuming a 44100 Hz sampling rate, the first 100 samples of the above magnitude of analytical signal are further multiplied by a piecewise linear weighting factor that is 1 for the first 20 samples and raises linearly to 5 for samples 21-100, to compensate for sound attenuation due to traveled distance. Other weighting factors, such as one following a second-order regime, can be used.

Figure 6:
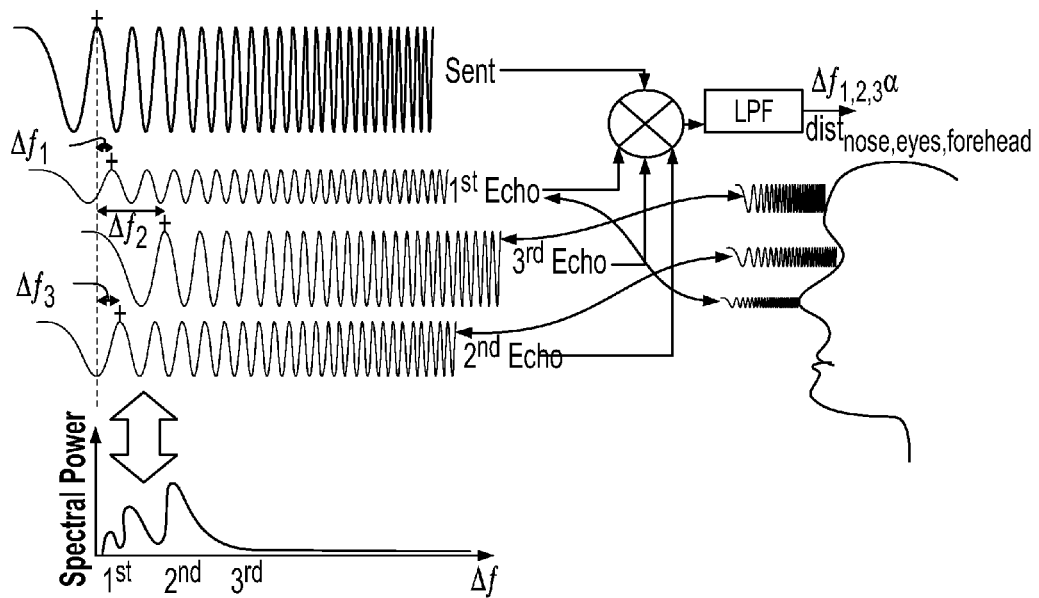
FIGS. 6 and 7 depict reflections from different facets of a face and a monitor screen, respectively.
Figure 7:
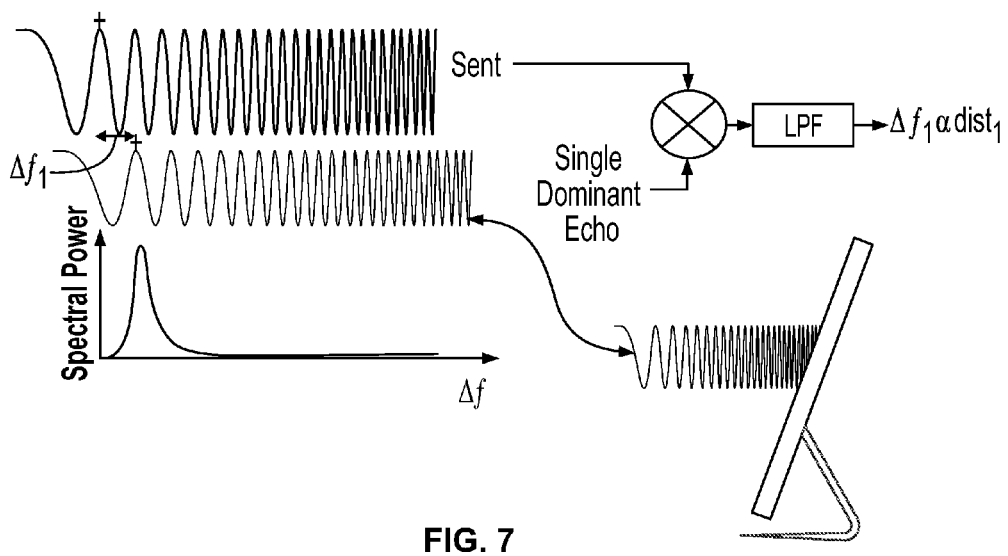

FIG. 6 depicts multiple reflections from different facets of a face (three samples are shown, using a CTFM technique). These echoes reveal the specific spatial face structures (as opposed to spoof signatures). This is due to the different delays (and magnitudes) of different sonic paths as detected by the demodulated sonic probe echoes. On the contrary, the spoofing display shown in FIG. 7 causes mostly a single, large peak during demodulation. Challenges can arise from low spatial resolution and high scattering of a typical face due to a 20 KHz upper frequency limitation imposed by the audio circuits of certain phones. Other challenges include variations caused by user behavior and background noise and motion/reflection artifacts induced by the uncontrolled environment, and overall low SNR due to device audio circuitry limitations, all addressed by the techniques described herein.

In some implementations, the feature set for the above-mentioned classifier is a collection of subsets selected for best classification performance using a random subset ensemble classification technique. The random subspace classifier ensemble can be, for example, a sum-rule-fused collection of k-nearest neighbor classifiers, or a sum-rule-fused collection of Support Vector Machines operating on a set of feature vectors of the decoded analytical signals. Appendices A and B provide classifiers and input spaces derived experimentally using a random subspace ensemble building methodology. Appendix A lists an example set of 80 feature vectors selected using a large training/testing dataset consisting of over 18,000 echoes recorded from real users, as well as various spoofing screens, using random subspace sampling in conjunction with kNN ensemble classifiers. The subspaces were obtained based on average cross validation performance (measured via ROC curve analysis) of different subspace configurations (i.e., input sample locations and dimensions, as well as the number of participating classifiers). The column location of each number shows the digital signal sample number from the decoded onset of chirp/coded signal transmission, using a sampling rate of 44100 Hz. In another implementation, the subspace ensemble is a collection of Support Vector Machine classifiers with Gaussian kernels receiving the set of 40 feature vectors of the decoded analytical signals listed in Appendix B, and selected as a subset of the 80 features in Appendix A based on their Fisher Discriminant Ratios (from Fisher Discriminant Linear classification using the larger dataset). Again, the column location of each number shows the digital signal sample number from the decoded onset of chirp/coded signal transmission, using a sampling rate of 44100 Hz.

To accurately identify the representations of specific faces (and not just generic faces vs. spoofs) in the echo space, in some implementations, the sonar classifier is trained to be subject-specific (and, possibly, device specific, as the following method accommodates the combined user-device peculiarities). This functionality can be achieved by training the classifier to distinguish the user's sonic features, garnered during biometric enrollment, against that of a representative impostor population (and not just spoofs, for subject specificity). Another advantage of this method is that the features gleaned during the enrollment also reflect the specifics of the device used for the enrollment and, thus, classifiers are adapted to the acoustic peculiarities of the specific device. The resulting user (and device) specific sonic pattern detector can be used as a part of a more precise, user (and device)-tuned anti-spoofing classifier, where this subject-specific classification is combined with the earlier mentioned spoof-detection classifier. In some implementations, the user-specific sonic profile detector itself can be used as a soft biometric.

The above acoustic interrogations of the ocular/facial biometric target can be enhanced by facial photometric responses to structured light imparted by scene interrogating mobile device, for better anti-spoofing. In some implementations, the structured light is in the form of coded intensity, coded color variations, coded spatial distribution, and/or coded phase variations of light imparted by the device, e.g. via embedded LCD or LED light sources. The aforesaid codes can be defined in terms of frequency regimes and specific maximal correlation sequences, such as Barker or M-sequences. In other implementations, the photometric profiles of the user's face are pre calculated based on generic population profiles of users vs. spoofs (user-agnostic photometric faceness).

Further, in some implementations, the 3D profiles of the user's face, as detected by photometric reflections of the user at the time of validated enrollment, are learned by classifiers for user-specificity. Along with sonic modality or on their own, these user specific portfolios can be used as soft biometrics which also induces more subject-specificity and, thus, accuracy into these anti-spoofing measures.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and can interact through a communication network. The relationship of client and server arises by virtue of computer programs running on the respective computers and having a client-server relationship to each other. A number of embodiments have been described. Nevertheless, it will be understood that various modifications may be made without departing from the spirit and scope of the invention.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language resource), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and can interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Appendix A

Feature Vector Set 1:
Classifier 1: 7, 9, 14, 15, 18, 20, 24, 27, 35, 37, 40, 45, 55, 58, 60, 64, 65, 70, 80, 81, 98, 100
Classifier 2: 6, 12, 13, 23, 26, 36, 44, 47, 50, 52, 58, 59, 63, 64, 67, 76, 77, 85, 86, 87, 89, 92
Classifier 3: 10, 21, 22, 25, 31, 32, 34, 37, 38, 46, 49, 62, 72, 73, 80, 82, 83, 84, 86, 90, 93, 95
Classifier 4: 1, 2, 5, 8, 15, 17, 20, 22, 23, 28, 29, 30, 41, 42, 51, 56, 61, 78, 83, 94, 96, 99
Classifier 5: 3, 4, 12, 16, 28, 30, 32, 37, 39, 43, 45, 54, 57, 60, 63, 66, 76, 78, 84, 87, 88, 97
Classifier 6: 4, 11, 13, 19, 27, 31, 39, 44, 47, 48, 49, 53, 58, 69, 71, 74, 75, 91, 93, 94, 99, 100
Classifier 7: 1, 2, 4, 6, 8, 9, 11, 13, 26, 33, 36, 41, 50, 51, 54, 67, 68, 69, 73, 79, 85, 90
Classifier 8: 10, 14, 17, 18, 19, 24, 33, 34, 36, 38, 41, 43, 52, 55, 59, 60, 68, 92, 93, 96, 98, 100

Classifier 9: 8, 17, 22, 23, 24, 25, 27, 30, 35, 40, 46, 56, 57, 62, 63, 70, 71, 72, 79, 88, 89, 99

Classifier 10: 3, 5, 9, 11, 29, 42, 58, 61, 62, 63, 66, 71, 75, 77, 80, 81, 82, 90, 94, 95, 96, 97

Classifier 11: 1, 3, 6, 14, 16, 21, 25, 32, 34, 35, 38, 39, 48, 49, 53, 55, 66, 70, 75, 78, 80, 97

Classifier 12: 7, 10, 15, 20, 24, 31, 33, 36, 40, 43, 44, 50, 52, 65, 67, 74, 76, 85, 91, 96, 98, 99

Classifier 13: 9, 16, 19, 20, 26, 41, 46, 47, 48, 49, 51, 68, 69, 73, 77, 82, 83, 84, 87, 89, 91, 95

Classifier 14: 2, 6, 8, 11, 18, 23, 26, 28, 29, 35, 38, 42, 45, 57, 61, 62, 64, 72, 88, 93, 96, 100

Classifier 15: 6, 12, 19, 20, 21, 37, 42, 43, 53, 54, 58, 59, 61, 70, 73, 74, 77, 78, 79, 83, 86, 93

Classifier 16: 3, 5, 6, 7, 18, 28, 30, 35, 39, 47, 51, 54, 55, 56, 65, 72, 82, 85, 86, 89, 90, 92

Classifier 17: 1, 2, 7, 31, 33, 34, 36, 39, 46, 56, 59, 64, 65, 66, 67, 69, 75, 79, 81, 86, 87, 92

Classifier 18: 9, 12, 13, 14, 15, 16, 17, 21, 27, 41, 44, 45, 49, 52, 57, 74, 76, 77, 81, 88, 91, 95

Classifier 19: 5, 17, 26, 29, 30, 45, 46, 48, 63, 65, 67, 68, 71, 72, 74, 75, 76, 88, 92, 96, 97, 98

Classifier 20: 1, 9, 13, 19, 21, 22, 25, 27, 37, 47, 50, 51, 53, 60, 61, 66, 70, 78, 79, 84, 95, 98

Classifier 21: 1, 2, 11, 12, 16, 18, 29, 32, 40, 42, 48, 50, 57, 62, 71, 73, 83, 84, 87, 90, 94, 100

Classifier 22: 3, 4, 7, 10, 15, 23, 25, 26, 31, 32, 33, 41, 43, 52, 56, 58, 76, 82, 88, 91, 92, 99

Classifier 23: 3, 4, 5, 7, 8, 12, 13, 22, 23, 33, 34, 38, 40, 44, 54, 60, 62, 63, 64, 89, 94, 97

Classifier 24: 10, 14, 15, 16, 20, 21, 27, 30, 42, 45, 47, 53, 68, 69, 72, 74, 79, 80, 81, 84, 89, 97

Classifier 25: 10, 11, 24, 28, 29, 32, 43, 44, 52, 64, 65, 66, 70, 71, 75, 77, 85, 87, 90, 94, 95, 100

Classifier 26: 5, 8, 16, 29, 33, 36, 37, 40, 52, 53, 54, 55, 56, 57, 59, 60, 69, 73, 82, 86, 91, 97

Classifier 27: 2, 5, 6, 12, 17, 22, 25, 34, 35, 39, 46, 48, 55, 59, 61, 64, 73, 75, 78, 79, 90, 99

Classifier 28: 2, 4, 9, 18, 24, 27, 31, 34, 36, 37, 42, 43, 44, 66, 78, 80, 81, 83, 85, 93, 96, 98

Classifier 29: 4, 5, 8, 13, 14, 17, 18, 19, 22, 26, 28, 38, 45, 46, 49, 51, 58, 60, 61, 72, 89, 93

Classifier 30: 20, 21, 27, 29, 31, 38, 40, 41, 50, 54, 58, 64, 65, 67, 68, 69, 81, 82, 92, 94, 98, 100

Classifier 31: 3, 4, 7, 9, 11, 19, 25, 26, 28, 30, 33, 53, 54, 55, 57, 65, 67, 71, 76, 80, 83, 86

Classifier 32: 2, 8, 10, 12, 14, 21, 23, 32, 35, 36, 47, 49, 56, 62, 69, 70, 77, 82, 84, 91, 95, 99

Classifier 33: 1, 14, 17, 18, 24, 28, 34, 39, 48, 51, 53, 59, 63, 67, 74, 85, 87, 88, 89, 95, 97, 100

Classifier 34: 3, 10, 11, 13, 15, 23, 28, 31, 35, 43, 46, 50, 51, 55, 60, 63, 68, 71, 77, 85, 88, 98

Classifier 35: 1, 6, 19, 38, 41, 42, 44, 45, 46, 47, 56, 57, 58, 61, 70, 73, 79, 81, 84, 90, 92, 100

Classifier 36: 16, 24, 25, 30, 32, 35, 37, 40, 48, 50, 52, 56, 64, 65, 66, 68, 72, 75, 76, 80, 87, 94

Classifier 37: 6, 7, 8, 39, 48, 54, 55, 57, 59, 63, 67, 74, 78, 79, 82, 86, 87, 89, 91, 93, 96, 99

Classifier 38: 4, 13, 15, 20, 23, 29, 31, 39, 40, 41, 42, 43, 47, 49, 50, 53, 59, 72, 73, 75, 82, 84

Classifier 39: 7, 15, 16, 17, 20, 22, 25, 27, 49, 51, 60, 62, 65, 76, 77, 80, 86, 91, 92, 93, 95, 97

Classifier 40: 1, 11, 14, 22, 24, 26, 28, 30, 35, 36, 38, 41, 49, 52, 56, 61, 78, 83, 90, 92, 96, 99

Classifier 41: 2, 9, 12, 18, 21, 30, 33, 34, 44, 47, 49, 61, 69, 71, 74, 76, 77, 81, 84, 85, 93, 94

Classifier 42: 3, 8, 12, 19, 22, 26, 31, 32, 42, 48, 50, 51, 64, 66, 67, 70, 79, 83, 87, 91, 98, 100

Classifier 43: 4, 6, 10, 21, 23, 34, 37, 44, 45, 46, 52, 55, 57, 58, 59, 60, 63, 68, 75, 78, 79, 94

Classifier 44: 2, 5, 7, 11, 13, 23, 24, 39, 41, 43, 57, 62, 70, 72, 74, 77, 80, 84, 88, 94, 97, 100

Classifier 45: 3, 5, 10, 14, 16, 21, 32, 33, 34, 39, 45, 64, 70, 73, 74, 83, 87, 88, 89, 90, 96, 99

Classifier 46: 10, 15, 18, 19, 20, 25, 26, 29, 40, 52, 55, 58, 62, 68, 78, 81, 85, 86, 89, 93, 96, 98

Classifier 47: 1, 8, 10, 15, 27, 30, 32, 33, 36, 38, 48, 53, 54, 66, 67, 69, 70, 71, 85, 95, 97, 98

Classifier 48: 2, 3, 5, 7, 9, 14, 22, 28, 43, 47, 50, 51, 53, 54, 65, 71, 73, 76, 81, 82, 83, 92

Classifier 49: 4, 6, 16, 17, 25, 31, 35, 41, 42, 45, 50, 51, 55, 62, 68, 77, 79, 80, 83, 86, 87, 95

Classifier 50: 1, 5, 9, 12, 13, 17, 18, 21, 24, 28, 37, 38, 39, 40, 61, 63, 69, 70, 73, 75, 82, 91

Classifier 51: 2, 3, 11, 15, 19, 26, 27, 29, 32, 34, 36, 37, 44, 48, 56, 59, 62, 66, 69, 71, 90, 93

Classifier 52: 8, 12, 14, 20, 22, 35, 47, 52, 54, 57, 60, 63, 64, 65, 69, 72, 78, 81, 84, 88, 91, 96

Classifier 53: 4, 8, 17, 29, 31, 42, 43, 46, 48, 53, 56, 58, 60, 61, 62, 65, 66, 68, 75, 76, 86, 94

Classifier 54: 7, 13, 15, 16, 19, 20, 21, 24, 25, 33, 36, 49, 70, 80, 86, 89, 90, 94, 95, 98, 99, 100

Classifier 55: 2, 6, 7, 10, 13, 18, 19, 22, 23, 29, 30, 40, 57, 58, 65, 66, 67, 72, 73, 88, 92, 99

Classifier 56: 1, 6, 9, 11, 18, 20, 27, 30, 38, 44, 59, 74, 75, 78, 82, 84, 85, 86, 89, 91, 92, 97

Classifier 57: 5, 12, 26, 33, 37, 38, 39, 42, 45, 46, 49, 52, 54, 56, 60, 66, 71, 73, 77, 90, 91, 94

Classifier 58: 6, 8, 16, 26, 28, 34, 35, 41, 44, 45, 46, 49, 50, 63, 68, 72, 79, 83, 87, 96, 97, 99

Classifier 59: 1, 4, 17, 23, 27, 29, 30, 31, 40, 43, 50, 51, 61, 64, 67, 68, 74, 76, 81, 93, 95, 100

Classifier 60: 2, 3, 11, 13, 23, 24, 25, 35, 47, 49, 52, 56, 57, 59, 71, 74, 75, 79, 81, 88, 96, 98

Classifier 61: 1, 7, 9, 12, 16, 17, 22, 32, 34, 36, 37, 46, 53, 72, 76, 77, 82, 85, 87, 88, 92, 95

Classifier 62: 3, 4, 11, 14, 17, 18, 22, 24, 25, 31, 50, 51, 54, 55, 57, 63, 78, 80, 87, 89, 92, 97

Classifier 63: 5, 6, 20, 21, 24, 32, 33, 36, 37, 38, 39, 43, 44, 46, 47, 60, 64, 66, 67, 69, 83, 90

Classifier 64: 7, 10, 14, 15, 19, 27, 28, 35, 40, 45, 48, 53, 54, 59, 61, 78, 82, 84, 85, 96, 98, 100

Classifier 65: 1, 8, 12, 15, 27, 29, 34, 40, 41, 44, 47, 52, 53, 55, 58, 59, 66, 70, 80, 89, 93, 97

Classifier 66: 2, 5, 6, 9, 10, 14, 26, 28, 31, 42, 43, 56, 60, 62, 63, 74, 80, 81, 90, 95, 98, 99

Classifier 67: 11, 13, 18, 20, 21, 27, 37, 38, 41, 42, 45, 51, 61, 62, 70, 76, 77, 82, 83, 88, 91, 93

Classifier 68: 2, 3, 9, 11, 12, 15, 19, 25, 27, 32, 36, 40, 49, 68, 69, 71, 72, 75, 85, 90, 98, 99

Classifier 69: 13, 16, 17, 18, 26, 29, 30, 32, 36, 39, 41, 46, 48, 55, 58, 61, 64, 65, 67, 79, 86, 100

Classifier 70: 1, 4, 23, 25, 30, 33, 34, 44, 45, 54, 60, 73, 77, 79, 84, 86, 89, 93, 94, 96, 98, 100

Classifier 71: 2, 4, 10, 13, 20, 22, 28, 34, 37, 38, 44, 45, 50, 58, 67, 69, 73, 81, 87, 91, 92, 94

Classifier 72: 8, 9, 11, 18, 19, 31, 47, 48, 54, 56, 57, 58, 62, 64, 68, 72, 74, 75, 84, 88, 97, 99

Classifier 73: 3, 4, 5, 21, 24, 33, 35, 40, 42, 43, 53, 55, 59, 63, 64, 65, 78, 83, 84, 85, 95, 97

Classifier 74: 7, 9, 16, 17, 20, 29, 32, 36, 39, 47, 51, 52, 53, 58, 59, 70, 71, 76, 80, 89, 93, 94

Classifier 75: 5, 10, 12, 14, 19, 23, 26, 33, 41, 44, 56, 57, 59, 60, 62, 69, 72, 75, 91, 92, 95, 99

Classifier 76: 22, 25, 31, 35, 38, 42, 43, 46, 50, 65, 66, 67, 78, 81, 83, 85, 86, 87, 89, 90, 97, 99

Classifier 77: 1, 2, 3, 8, 10, 11, 37, 49, 54, 61, 63, 66, 68, 69, 71, 75, 76, 77, 78, 79, 83, 100

Classifier 78: 1, 5, 8, 14, 20, 23, 24, 26, 28, 32, 35, 39, 46, 48, 52, 53, 55, 73, 80, 84, 88, 93

Classifier 79: 3, 6, 7, 14, 16, 21, 29, 30, 37, 47, 52, 55, 60, 61, 62, 70, 74, 79, 81, 82, 92, 100

Classifier 80: 7, 15, 22, 25, 31, 34, 35, 36, 41, 44, 45, 48, 49, 51, 53, 56, 72, 73, 77, 80, 81, 82

Appendix B

Feature Vector Set 2:

Classifier 1: 7, 9, 14, 15, 18, 20, 24, 27, 35, 37, 40, 45, 55, 58, 60, 64, 65, 70, 80, 81, 98, 100

Classifier 2: 1, 2, 5, 8, 15, 17, 20, 22, 23, 28, 29, 30, 41, 42, 51, 56, 61, 78, 83, 94, 96, 99

Classifier 3: 3, 4, 12, 16, 28, 30, 32, 37, 39, 43, 45, 54, 57, 60, 63, 66, 76, 78, 84, 87, 88, 97

Classifier 4: 4, 11, 13, 19, 27, 31, 39, 44, 47, 48, 49, 53, 58, 69, 71, 74, 75, 91, 93, 94, 99, 100

Classifier 5: 1, 2, 4, 6, 8, 9, 11, 13, 26, 33, 36, 41, 50, 51, 54, 67, 68, 69, 73, 79, 85, 90

Classifier 6: 3, 5, 9, 11, 29, 42, 58, 61, 62, 63, 66, 71, 75, 77, 80, 81, 82, 90, 94, 95, 96, 97

Classifier 7: 7, 10, 15, 20, 24, 31, 33, 36, 40, 43, 44, 50, 52, 65, 67, 74, 76, 85, 91, 96, 98, 99

Classifier 8: 2, 6, 8, 11, 18, 23, 26, 28, 29, 35, 38, 42, 45, 57, 61, 62, 64, 72, 88, 93, 96, 100

Classifier 9: 3, 5, 6, 7, 18, 28, 30, 35, 39, 47, 51, 54, 55, 56, 65, 72, 82, 85, 86, 89, 90, 92

Classifier 10: 5, 17, 26, 29, 30, 45, 46, 48, 63, 65, 67, 68, 71, 72, 74, 75, 76, 88, 92, 96, 97, 98

Classifier 11: 3, 4, 7, 10, 15, 23, 25, 26, 31, 32, 33, 41, 43, 52, 56, 58, 76, 82, 88, 91, 92, 99

Classifier 12: 3, 4, 5, 7, 8, 12, 13, 22, 23, 33, 34, 38, 40, 44, 54, 60, 62, 63, 64, 89, 94, 97

Classifier 13: 5, 8, 16, 29, 33, 36, 37, 40, 52, 53, 54, 55, 56, 57, 59, 60, 69, 73, 82, 86, 91, 97

Classifier 14: 2, 5, 6, 12, 17, 22, 25, 34, 35, 39, 46, 48, 55, 59, 61, 64, 73, 75, 78, 79, 90, 99

Classifier 15: 2, 4, 9, 18, 24, 27, 31, 34, 36, 37, 42, 43, 44, 66, 78, 80, 81, 83, 85, 93, 96, 98

Classifier 16: 4, 5, 8, 13, 14, 17, 18, 19, 22, 26, 28, 38, 45, 46, 49, 51, 58, 60, 61, 72, 89, 93

Classifier 17: 3, 4, 7, 9, 11, 19, 25, 26, 28, 30, 33, 53, 54, 55, 57, 65, 67, 71, 76, 80, 83, 86

Classifier 18: 4, 13, 15, 20, 23, 29, 31, 39, 40, 41, 42, 43, 47, 49, 50, 53, 59, 72, 73, 75, 82, 84

Classifier 19: 4, 6, 10, 21, 23, 34, 37, 44, 45, 46, 52, 55, 57, 58, 59, 60, 63, 68, 75, 78, 79, 94

Classifier 20: 2, 5, 7, 11, 13, 23, 24, 39, 41, 43, 57, 62, 70, 72, 74, 77, 80, 84, 88, 94, 97, 100

Classifier 21: 3, 5, 10, 14, 16, 21, 32, 33, 34, 39, 45, 64, 70, 73, 74, 83, 87, 88, 89, 90, 96, 99

Classifier 22: 2, 3, 5, 7, 9, 14, 22, 28, 43, 47, 50, 51, 53, 54, 65, 71, 73, 76, 81, 82, 83, 92

Classifier 23: 4, 6, 16, 17, 25, 31, 35, 41, 42, 45, 50, 51, 55, 62, 68, 77, 79, 80, 83, 86, 87, 95

Classifier 24: 1, 5, 9, 12, 13, 17, 18, 21, 24, 28, 37, 38, 39, 40, 61, 63, 69, 70, 73, 75, 82, 91

Classifier 25: 4, 8, 17, 29, 31, 42, 43, 46, 48, 53, 56, 58, 60, 61, 62, 65, 66, 68, 75, 76, 86, 94

Classifier 26: 2, 6, 7, 10, 13, 18, 19, 22, 23, 29, 30, 40, 57, 58, 65, 66, 67, 72, 73, 88, 92, 99

Classifier 27: 5, 12, 26, 33, 37, 38, 39, 42, 45, 46, 49, 52, 54, 56, 60, 66, 71, 73, 77, 90, 91, 94

Classifier 28: 1, 4, 17, 23, 27, 29, 30, 31, 40, 43, 50, 51, 61, 64, 67, 68, 74, 76, 81, 93, 95, 100

Classifier 29: 1, 7, 9, 12, 16, 17, 22, 32, 34, 36, 37, 46, 53, 72, 76, 77, 82, 85, 87, 88, 92, 95

Classifier 30: 3, 4, 11, 14, 17, 18, 22, 24, 25, 31, 50, 51, 54, 55, 57, 63, 78, 80, 87, 89, 92, 97

Classifier 31: 5, 6, 20, 21, 24, 32, 33, 36, 37, 38, 39, 43, 44, 46, 47, 60, 64, 66, 67, 69, 83, 90

Classifier 32: 7, 10, 14, 15, 19, 27, 28, 35, 40, 45, 48, 53, 54, 59, 61, 78, 82, 84, 85, 96, 98, 100

Classifier 33: 2, 5, 6, 9, 10, 14, 26, 28, 31, 42, 43, 56, 60, 62, 63, 74, 80, 81, 90, 95, 98, 99

Classifier 34: 2, 3, 9, 11, 12, 15, 19, 25, 27, 32, 36, 40, 49, 68, 69, 71, 72, 75, 85, 90, 98, 99

Classifier 35: 1, 4, 23, 25, 30, 33, 34, 44, 45, 54, 60, 73, 77, 79, 84, 86, 89, 93, 94, 96, 98, 100

Classifier 36: 2, 4, 10, 13, 20, 22, 28, 34, 37, 38, 44, 45, 50, 58, 67, 69, 73, 81, 87, 91, 92, 94

Classifier 37: 3, 4, 5, 21, 24, 33, 35, 40, 42, 43, 53, 55, 59, 63, 64, 65, 78, 83, 84, 85, 95, 97

Classifier 38: 7, 9, 16, 17, 20, 29, 32, 36, 39, 47, 51, 52, 53, 58, 59, 70, 71, 76, 80, 89, 93, 94

Classifier 39: 5, 10, 12, 14, 19, 23, 26, 33, 41, 44, 56, 57, 59, 60, 62, 69, 72, 75, 91, 92, 95, 99

Classifier 40: 1, 5, 8, 14, 20, 23, 24, 26, 28, 32, 35, 39, 46, 48, 52, 53, 55, 73, 80, 84, 88, 93

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:
emitting, using an audio output component of a user device, one or more audio signals;
receiving, using an audio input component of the user device, one or more reflections of the audio signals off a target;
determining, based on the one or more reflections, whether the target comprises at least one of a face-like structure and face-like tissue;
receiving a plurality of images of the target;
identifying, based on the images, whether the target has a first pulse;
measuring a second pulse of the target through physical contact with the target; and
determining whether the target is a spoof based at least in part on (i) the determination of whether the target comprises at least one of a face-like structure and face-like tissue, (ii) the identification of whether the target has a pulse, and (iii) the measurement of the second pulse.

2. The method of claim 1, wherein the user device is a mobile device comprising a smartphone, a tablet, or a laptop.

3. The method of claim 1, wherein the one or more audio signals comprise short coded pulse pings, short term chirps, or CTFM pings.

4. The method of claim 1, further comprising:
training a classifier to identify physical features of the target; and
providing, as input to the classifier, information based on the one or more reflections of the audio signals off the target,
wherein the determination of whether the target is a spoof is further based at least in part on an output of the classifier received in response to the provided input.

5. The method of claim 1, further comprising randomizing one or more characteristics of the one or more audio signals.

6. The method of claim 1, further comprising:
receiving a plurality of images of the target; and
determining, based on detected light reflections in the images, whether the target comprises a three-dimensional face-like structure.

7. The method of claim 1, wherein the first pulse is identified using remote photoplethysmography.

8. The method of claim 1, further comprising determining whether the second pulse correlates to the first pulse, wherein the determination of whether the target is a spoof is further based at least in part on the correlation.

9. The method of claim 1, wherein measuring the second pulse comprises receiving information associated with the second pulse from the user device or another handheld or wearable device.

10. The method of claim 9, wherein the information associated with the second pulse comprises a ballistocardiographic signal.

11. A system comprising:
at least one memory for storing computer-executable instructions;
at least one processing unit for executing the instructions stored on the memory, wherein execution of the instructions programs the at least one processing unit to perform operations comprising:
emitting, using an audio output component of a user device, one or more audio signals;
receiving, using an audio input component of the user device, one or more reflections of the audio signals off a target;
determining, based on the one or more reflections, whether the target comprises at least one of a face-like structure and face-like tissue;
receiving a plurality of images of the target;
identifying, based on the images, whether the target has a first pulse;
measuring a second pulse of the target through physical contact with the target; and
determining whether the target is a spoof based at least in part on (i) the determination of whether the target comprises at least one of a face-like structure and face-like tissue, (ii) the identification of whether the target has a pulse, and (iii) the measurement of the second pulse.

12. The system of claim 11, wherein the user device is a mobile device comprising a smartphone, a tablet, or a laptop.

13. The system of claim 11, wherein the one or more audio signals comprise short coded pulse pings, short term chirps, or CTFM pings.

14. The system of claim 11, wherein the operations further comprise:
training a classifier to identify physical features of the target; and
providing, as input to the classifier, information based on the one or more reflections of the audio signals off the target,
wherein the determination of whether the target is a spoof is further based at least in part on an output of the classifier received in response to the provided input.

15. The system of claim 11, wherein the operations further comprise randomizing one or more characteristics of the one or more audio signals.

16. The system of claim 11, wherein the operations further comprise:
receiving a plurality of images of the target; and
determining, based on detected light reflections in the images, whether the target comprises a three-dimensional face-like structure.

17. The system of claim 11, wherein the first pulse is identified using remote photoplethysmography.

18. The system of claim 11, wherein the operations further comprise determining whether the second pulse correlates to the first pulse, wherein the determination of whether the target is a spoof is further based at least in part on the correlation.

19. The system of claim 11, wherein measuring the second pulse comprises receiving information associated with the second pulse from the user device or another handheld or wearable device.

20. The system of claim 19, wherein the information associated with the second pulse comprises a ballistocardiographic signal.

21. A non-transitory computer-readable medium having instructions stored thereon that, when executed, program at least one processor to perform operations comprising:
emitting, using an audio output component of a user device, one or more audio signals;
receiving, using an audio input component of the user device, one or more reflections of the audio signals off a target;
determining, based on the one or more reflections, whether the target comprises at least one of a face-like structure and face-like tissue;
receiving a plurality of images of the target;

identifying, based on the images, whether the target has a first pulse;

measuring a second pulse of the target through physical contact with the target; and determining whether the target is a spoof based at least in part on (i) the determination of whether the target comprises at least one of a face-like structure and face-like tissue, (ii) the identification of whether the target has a pulse, and (iii) the measurement of the second pulse.

* * * * *